United States Patent
Toole et al.

(10) Patent No.: US 12,171,951 B2
(45) Date of Patent: Dec. 24, 2024

(54) TACTILE STIMULUS RELAXATION PLATFORM

(71) Applicants: Beth Toole, Oromocto (CA); Trevor Toole, Oromocto (CA)

(72) Inventors: Beth Toole, Oromocto (CA); Trevor Toole, Oromocto (CA)

( * ) Notice: Subject to any disclaimer, the term of this patent is extended or adjusted under 35 U.S.C. 154(b) by 920 days.

(21) Appl. No.: 17/233,615

(22) Filed: Apr. 19, 2021

(65) Prior Publication Data
US 2022/0193365 A1  Jun. 23, 2022

Related U.S. Application Data

(60) Provisional application No. 63/128,894, filed on Dec. 22, 2020.

(51) Int. Cl.
*A61M 21/02* (2006.01)
*A61M 21/00* (2006.01)

(52) U.S. Cl.
CPC ..... *A61M 21/02* (2013.01); *A61M 2021/0016* (2013.01); *A61M 2021/0022* (2013.01); *A61M 2205/3576* (2013.01)

(58) Field of Classification Search
CPC .......... A61M 21/02; A61M 2021/0016; A61M 2021/0022; A61M 2205/3576
See application file for complete search history.

(56) References Cited

U.S. PATENT DOCUMENTS

| | | | |
|---|---|---|---|
| 2002/0084904 A1* | 7/2002 | De La Huerga | G06K 19/07762 340/573.4 |
| 2010/0253468 A1* | 10/2010 | Devecka | B43K 23/00 340/3.1 |
| 2019/0019573 A1* | 1/2019 | Lake | G16H 80/00 |
| 2019/0339654 A1* | 11/2019 | Edwards | A61L 9/035 |

FOREIGN PATENT DOCUMENTS

CN          107968870 A  *  4/2018

\* cited by examiner

*Primary Examiner* — Thaddeus B Cox
*Assistant Examiner* — Joshua Daryl D Lannu
(74) *Attorney, Agent, or Firm* — Brennan, Manna & Diamond, LLC

(57) ABSTRACT

This present invention relates to a tactile sensory relaxation platform or card preferably having between two and ten different tactile objects affixed to at least one of its surfaces. The relaxation platform/card allows individuals suffering from anxiety, PTSD, panic attacks and the like to alleviate stress, anxiety, panic and other mental health conditions and avoid engaging in dangerous or undesirable activities. More specifically, the individual may touch or rub the affixed tactile objects themselves from negative thoughts and refocus their attention on the objects.

17 Claims, 3 Drawing Sheets

TACTILE STIMULUS RELAXATION PLATFORM

CROSS-REFERENCE TO RELATED APPLICATION

The present application claims priority to, and the benefit of, U.S. Provisional Application No. 63/128,894, which was filed on Dec. 22, 2020 and is incorporated herein by reference in its entirety.

FIELD OF THE INVENTION

The present invention relates generally to the field of stress relieving accessories. More specifically, the present invention relates to a tactile sensory device to help the user feel better and relaxed both when using the device and immediately thereafter. The relaxation platform, such as a card, preferably comprises between two and ten different tactile or sensory objects affixed to or otherwise integrated with the surface of the card. The card allows the users to touch and rub the affixed tactile or sensory objects to cope with anxiety, post-traumatic stress disorder (PTSD), anger and other emotional or mental health conditions. The card of the present invention can be used to redirect the attention of the user from negative thoughts to the tactile objects, and thereby helps in alleviating stress, anxiety, panic and other similar conditions. In this manner, the card/platform helps contribute towards improving the overall mental health of the individual utilizing the same. Accordingly, the present disclosure makes specific reference thereto. Nonetheless, it is to be appreciated that aspects of the present invention are also equally applicable to other like applications, devices and methods of manufacture.

BACKGROUND OF THE INVENTION

By way of background, people around the world are becoming more aware of the importance of mental health. Mental health is important at every stage of life, from childhood and adolescence through adulthood and aging. Mental health includes emotional, psychological, and social well-being, and helps an individual to think clearly, address feelings and participate more fully and actively in life. Many people may suffer from issues such as anxiety, PTSD, panic attacks, etc. due to various reasons such as stress, pressure, tragic events, or other traumatic events. The genetic make-up of an individual may also contribute to the level of emotional well-being of that individual. Some people may be unable to relax or engage in everyday activities, which may lead them to do something impulsive or to draw unwanted attention to themselves, thereby affecting the mental health of some individuals.

The most common mental health conditions are anxiety and mood disorders. More than 18% of adults each year struggle with some type of anxiety disorder, including post-traumatic stress disorder (PTSD), obsessive-compulsive disorder (OCD), panic disorder (panic attacks), generalized anxiety disorder and other specific phobias. Statistically, nearly 19% of the adult population, 46% of teenagers and 13% of children are affected by mental health issues each year. Struggling with mental health can lead to destructive behaviors for people, potentially ending in tragedy or other negative behaviors. People may be unable to focus on certain tasks and end up stressed-out rather than successfully completing their goals, jobs or activities.

To overcome feelings of anxiety, post-traumatic stress disorder (PTSD), uncontrolled anger, and other mental health conditions, people may seek the help of or treatment from mental health professionals, who may advise patients to undergo pharmaceutical treatment and/or traditional counseling or therapy. The course of treatment may be of a long duration to be effective and may become quite expensive as well. Appointments, medical tests, medicines and other expenses may be too costly for most people, depending on their insurance coverage and/or ability to pay. People who are unable to afford such costly medical treatments may be prone to give up the treatment before the full regimen is over, thereby rendering it ineffective. Additionally, the pharmaceutical treatment may have different side-effects on some patients, which may cause discomfort and inconvenience to the individual undergoing the treatment. Apart from pharmaceutical treatment, people may also be advised to undergo psychotherapy, lifestyle changes and even homeopathic remedies. However, it is difficult for many people to distract themselves from negative thoughts in order to alleviate stress, anxiety, panic, and other conditions in situations where mental health professionals are not immediately accessible. People may seek cost-effective, safe methods to overcome stress, anxiety, and other similar mental health-related issues.

Therefore, there exists a long felt need in the art for a stress relieving product or accessory that an individual can use in order to reduce the individual's stress, anxiety, panic and other similar conditions. There is also a long felt need in the art for an anxiety relieving and stress reducing product that is specially designed for people suffering from anxiety, post-traumatic stress disorder (PTSD), anger, and other mental or psychological health conditions. Additionally, there is a long felt need in the art for a stress relieving or reducing product that is easily portable and that can be conveniently transported and immediately available when required by the user. Moreover, there is a long felt need in the art for a stress relieving or reducing accessory that is cost-effective, affordable and easily replicable/reproducible. Furthermore, there is a long felt need in the art for a stress relieving or reducing product that is non-medicating and that does not produce any physical side effects in the user, and that can be easily and successfully used and adopted by all age groups. Finally, there is a long felt need in the art for a stress reducing or relieving product that distracts the mind of an individual from negative thoughts or other urges to engage in disruptive behaviors.

The subject matter disclosed and claimed herein, in one embodiment thereof, comprises a handheld, physical relaxation platform or card with a plurality of attached tactile or sensory objects to alleviate stress, anxiety and/or panic in an individual. In one embodiment, the platform comprises a substantially rectangular card made of a pliable plastic having first and second sides, with a roughened rear or second side having a plurality of tactile or other sensory objects of different textures, shapes and sizes. A glossy or shiny first or front surface has one or more logos or prints as well as personal information relating to the carrier, such as an emergency contact number or other essential information or procedures. The platform/card may include one or more cut-outs or slots for attaching a keychain or other accessories. The tactile or other sensory objects attached to the card may include, for example and without limitation, a button, a heart-shaped tactile surface, a lightweight natural gemstone, a rough surface, a cylindrical tactile surface with edges, a lightweight pearl like material, three protruding soothing surfaces and a cut-out area or slot.

In this manner, the novel sensory platform/card of the present invention accomplishes all of the forgoing objectives, and provides a relatively safe, easy, convenient and cost-effective solution to helping an individual reduce, relieve and overcome anxiety, panic, stress and other similar symptoms. The sensory platform card of the present invention is also user-friendly, inasmuch as it is less expensive than alternatives, does not produce side-effects in the individual users and can be customized to meet each individual's needs and/or preferences. Additionally, the tactile and sensory card of the present invention offers a way for both children and adults to refocus themselves by alleviating stress, anxiety, panic, and other similar conditions.

SUMMARY OF THE INVENTION

The following presents a simplified summary in order to provide a basic understanding of some aspects of the disclosed innovation. This summary is not an extensive overview, and it is not intended to identify key or critical elements or to delineate the scope thereof. Its sole purpose is to present some general concepts in a simplified form as a prelude to the more detailed description that is presented later.

The subject matter disclosed and claimed herein, in one embodiment thereof, comprises a handheld physical relaxation platform, card or element with attached tactile or other sensory objects to alleviate stress, anxiety and/or panic of a user. The card or element, in one embodiment, includes a substantially rectangular card of semi-rigid, yet pliable plastic having two opposing sides. A glossy front or first side or surface has one or more logos or prints, and one cut-out area or slot for attaching a keychain or other accessories. The front or first side may also contain personalized or emergency information relating to the individual user. A rough rear or second side has a plurality of tactile objects of different textures, shapes and sizes. The number of different objects may be from two to ten different items. The tactile objects may include, for example, a button, a heart-shaped tactile surface, a lightweight natural gemstone, a rough surface, a cylindrical tactile surface having edges, a lightweight pearl like material, three protruding soothing surfaces and a cut-out slot.

In a further embodiment of the present invention, a tactile and sensory card having a plurality of attached or associated tactile objects is disclosed. The tactile card is designed to distract an individual from having negative thoughts or engaging in disruptive behaviors. In one embodiment, the tactile card comprises a substantially rectangular structure having curved edges, and a plurality of tactile objects of different textures, shapes and hardness that are attached to one of the sides or surfaces of the card, wherein printed or imaged logos and other useful information may be provided on the other surface or side of the card. An accompanied essential oil may also be provided to apply to one or more of the tactile objects to increase the sensitivity and efficiency of the same and to appeal to the senses of a user touching, sliding or pressing the surfaces of the tactile objects.

In yet a further embodiment of the present invention, a method of using a handheld card with attached tactile objects to distract an individual from having negative thoughts, engaging in disruptive behaviors or other unacceptable activities, and to refocus the attention of the individual is disclosed. The method comprises the initial steps of holding the handheld small card in the individual's hand or placing the card on a surface, and then touching, sliding or pressing the surfaces of the tactile objects attached to the card to focus the individual's attention on the tactile objects, as opposed to on any negative thoughts, behaviors and/or stress. An additional step of applying an essential oil on the surface of one or more of the tactile objects may be done to appeal to the senses of the individual, and to increase the soothing properties and positive energy directed towards the individual.

In one embodiment, the tactile objects are permanently attached to the tactile or sensory card to increase the durability and useful life of the same. Alternatively, the tactile objects may be removably attached so that a user can remove the objects not desired by the user, and replace them with the other desired or more effective tactile objects. In this manner, the specific individual may customize his or her card to address the particular condition of the individual, or throughout changing stages of the treatment of the individual.

In yet a further embodiment of the present invention, a kit for creating and maintaining a sensory card is disclosed and includes a package configured for either retail sale or on-line delivery. In the preferred embodiment, the kit comprises at least one card having a front and a rear surface, a plurality of tactile elements for attachment to the card and one or more means of attaching the tactile objects to the card. The plurality of tactile elements may be attached to the card by at least one of a mechanical fastener, adhesive, etc. In one embodiment, the kit may further comprise one or more essential oils or the same may be purchased separately. The essential oils may further comprise a fragrance and/or an emollient, and the card can be available in flow wrap pouches or individual sachets or boxes.

In a still further embodiment of the present invention, a relaxation platform is disclosed and includes a shaped element having a central area and a perimeter. The central area has a front surface and a rear surface and a plurality of shaped items with at least two with different shape configurations. All of the plurality of shaped items are within the perimeter on the rear surface. At least one slot for holding an accessory attached to the shaped element is preferably located along the front surface.

The tactile stimulus relaxation platform or "feel better" card of the present invention is advantageous as it provides a portable, relatively lightweight and inexpensive alternative to bulky and expensive toys or gadgets for providing relief from anger, stress or anxiety. The platform/card can be used by individuals of any age to refocus themselves and alleviate their stress, panic, anxiety and other mental or physical conditions. More specifically, the platform/card can be easily carried in a pocket, purse or attached to a keychain, wherein the tactile objects are touched, rubbed and pressed by an individual to cope with his or her anxiety, PTSD, anger and/or other mental health conditions.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE INVENTION

Figure 1:
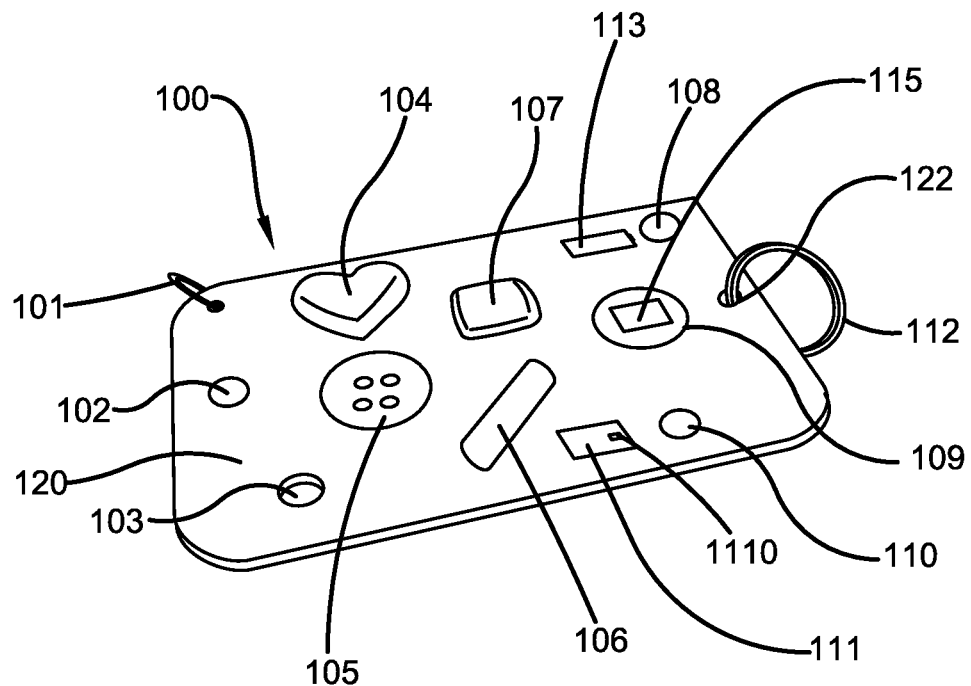
FIG. 1 illustrates a rear perspective view of one potential embodiment of the tactile platform or card of the present invention in accordance with the disclosed architecture, wherein a plurality of tactile objects are attached thereto in spaced-apart fashion.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a tactile platform or card that an individual can use in order to reduce the individual's stress, anxiety, panic and other similar conditions. There is also a long felt need in the art for a tactile platform or card that is specially designed for people suffering from anxiety, post-traumatic stress disorder (PTSD), anger, and other mental or psychological health conditions. Additionally, there is a long felt need in the art for a stress relieving or reducing tactile platform or card that is easily portable and that can be conveniently transported and immediately available when required by the user. Moreover, there is a long felt need in the art for a stress relieving or reducing tactile platform or card that is cost-effective, affordable and easily replicable/reproducible. Furthermore, there is a long felt need in the art for a tactile platform or card that is non-medicating and that does not produce any physical side effects in the user, and that can be easily and successfully used and adopted by all age groups. Finally, there is a long felt need in the art for a stress reducing or relieving a tactile platform or card that distracts the mind of an individual from negative thoughts or other urges to engage in disruptive behaviors.

The present invention, in one exemplary embodiment, is a novel handheld physical platform or card having a plurality of attached or integral tactile objects to alleviate or reduce stress, anxiety and panic of the user. The novel platform or card includes a substantially rectangular or other shaped card of pliable plastic having a front and a rear side. The front surface is relatively glossy in appearance and has one or more logos, indicia and prints, and one or more cut-outs or slots for attaching a keychain or other accessories. By comparison, the relatively rough rear side has a plurality of tactile objects of different textures, shapes and sizes positioned thereon in spaced-apart fashion. The tactile objects may include, but are not limited to, a button, a heart-shaped tactile surface, a lightweight natural gemstone, a rough surface, a cylindrical tactile surface with edges, a lightweight pearl-like material, three protruding soothing surfaces and a cut-out slot.

Referring initially to the drawings, FIG. 1 illustrates a rear perspective view of one potential embodiment of the tactile platform or card 100 of the present invention in accordance with the disclosed architecture, wherein a plurality of tactile objects are attached thereto in spaced-apart fashion. As shown, the tactile platform/card 100 is preferably similar in size and shape to a conventional greeting card, but can be of any shape or size that satisfies user need and/or preference. The card 100 is comprised of a plurality of different tactile objects which may be of various sizes, shapes and designs and have various textures to appeal to different senses of an individual touching or otherwise interacting with the tactile objects. The tactile objects are preferably affixed to one face of the card 100. In the present embodiment, there are ten tactile objects affixed to the rear side 120 of the card 100 with an adhesive. Alternatively, the tactile objects may be attached to the rear surface by a mechanical fastener such as a hook and loop fastener, snap, button or the like to allow the objects to be removed and replaced with other items. The tactile objects can be made up of various different materials, colors and textures, as described more fully below.

In the present embodiment, a slot or other opening 122 for a key chain 112 or other accessory is present to easily transport the card 100. The tactile objects may also include one or more of the following: a smooth heart-shaped tactile surface 104; a lightweight natural gemstone 107 having physical, emotional and spiritual healing powers for recuperating from a variety of physical and mental illnesses; a rough surface 109 to appeal to the senses of a user upon touching the rough surface 109; a generally cylindrically-shaped tactile surface 106 with edges that can be pressed to give calmness to a user; a lightweight pearl like material 101; a curved button 105 with openings therein; and three protruding soothing surfaces 102, 108, 110 of approximately the same or different sizes to provide soothing sensations to a user touching said surfaces. The surfaces 102, 108, 110 are preferably comprised of a plastic/silicone hybrid material that feels smooth to the touch. A cut-out slot 103 may also be provided that allows the individual to stick his or her finger into the slot 103 to relax.

All the tactile objects described above are preferably affixed to the rear surface 120 of the card 100, and can be of different sizes and placed at different positions along the rear surface 120 in spaced apart relationship to one another. The tactile platform/card 100 may further comprise a speaker 111 which can play soothing sounds or voices for the individual to hear in order to help alleviate the anxiety the person may be experiencing. The speaker 111 may have a memory unit or module 1110 to play different sounds or voices, and a battery 113 to provide the energy for the speaker 111 to play and emit the sounds. The battery 113 may also provide energy to drive a vibratory device 115 so that the individual can experience vibrations to further soothe the individual.

The various tactile objects soothe a user through his or her sensory needs. In one embodiment, the lightweight natural gemstone 107 can be made up of an obsidian gemstone or a Moroccan selenite crystal. Some of the tactile objects may also be scented with a blend of self-regulating herbs and spices (e.g., lavender, peppermint, cinnamon, cloves, etc.) to provide a soothing aroma to the user.

By touching, rubbing and/or pressing the various tactile objects affixed to the rear surface 120 of the card 100, the individual will engage both his or her fingers as well as his or her mind, and thereby redirect their attention to the tactile objects rather than negative thoughts or engaging in unhealthy or disruptive behavior in their environment. The platform/card 100 also allows the individual to touch, rub and/or press upon the various tactile objects in an effort to cope with the individual's anxiety, PTSD, anger and other mental health conditions. The platform/card 100 is preferably comprised of a relatively pliable plastic, but may also be fully rigid. The platform/card 100 may also be palm-shaped so as to easily fit in the hand of the individual using the same.

Additionally, it should be appreciated that the number of tactile objects can be more or less than those specified above to satisfy the user's needs and/or preferences. Also, there can be more than one of the same tactile object if the object helps a particular user more than another different type of object. In one embodiment, tactile objects 101, 107 are sensory "worry stones" that help a user feel more relaxed and better focused.

Figure 2:
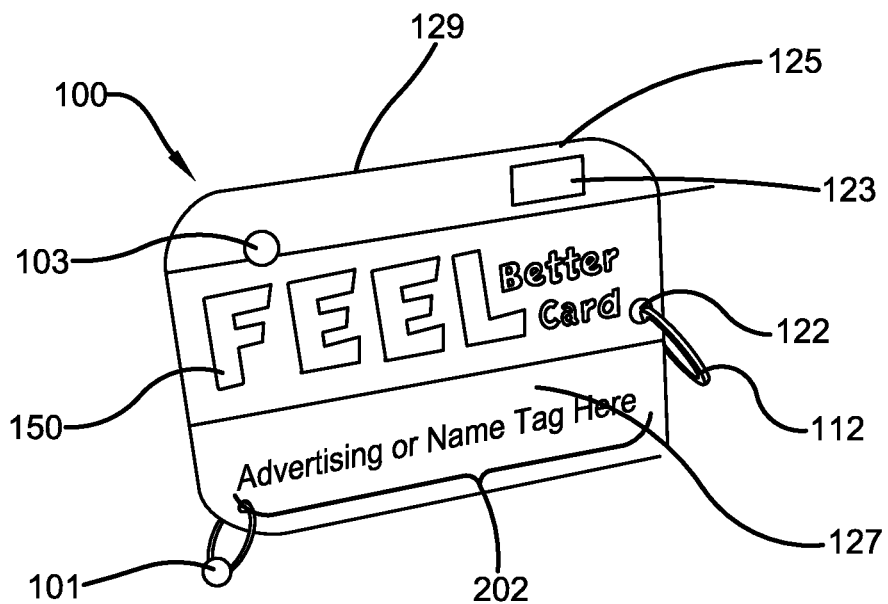
FIG. 2 illustrates a front perspective view of one potential embodiment of the tactile platform or card of the present invention in accordance with the disclosed architecture, wherein the a plurality of accessories or other information is placed thereon or attached thereto.

FIG. 2 illustrates a front perspective view of one potential embodiment of the tactile platform or card 100 of the present invention in accordance with the disclosed architecture, wherein a plurality of accessories or other information is placed thereon or attached thereto. The front surface or first side 150 of the platform/card 100 may have marketing information thereon, as well as other indicia or information such as, but not limited to, emergency treatment or contact information in the event of a panic attack or other similar debilitating condition. On the bottom half of the front surface 150, a logo, trademark, name of a company or any other design 202 can be printed or embossed. The card 100 may also contain an electronic chip 123 that may be read by a chip reader or smart phone having, for example, an NFC reader so that additional information may be retrieved which can be used to assist the user, either by contacting a health care professional or other emergency contact, and providing them with critical treatment information.

The front surface 150 of the platform/card 100 further comprises a slot or other opening 103, a key chain slot 122 and slot for a lightweight pearl-like material 101, or other desired accessories. The front surface 150 may not have any affixed tactile objects, and preferably has a relatively smooth surface so as to conceal the tactile objects and elements on the rear side 120. The front surface 150 can also be customized as per the marketing and/or branding strategy of any business or prescribed treatment elements from a healthcare provider. The platform/card 100 may further comprise a perimeter 129 and a relatively soft and compressible foam material 125 disposed about the central portion 127 of the card. The compressible material 125 may also be integrated with the platform/card 100 to create a core 127 that is rigid, and an outer area which is compressible. The compressible material 125 may be selected from a polyurethane foam, rubber, latex or any other similar material.

Figure 3:
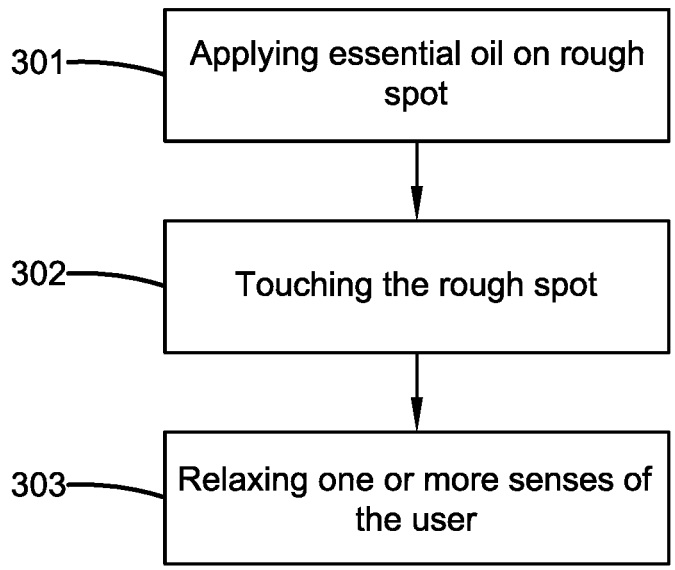
FIG. 3 illustrates a flow diagram of one potential method of using the tactile platform or card of the present invention to cope with an individual's anxiety, PTSD, anger and other mental health conditions in accordance with the disclosed architecture.

FIG. 3 illustrates a flow diagram of one potential method of using the tactile platform or card 100 of the present invention to cope with an individual's anxiety, PTSD, anger and/or other mental health conditions in accordance with the disclosed architecture. At Block 301, a few drops of an essential oil derived from plants, flowers and/or fruits is applied on the rough spot 109 to increase the sensory power of the rough spot/tactile object 109. Further, the rough spot 109 may include an absorptive patch or reservoir 115 to hold the essential oil for longer periods of time and to allow continued dispersing of the oils. In one embodiment, the essential oil may be a bergamot orange, chamomile, clary sage, lavender, neroli, peppermint, spearmint, rosemary, cedarwood, sandalwood, tea tree or any combination thereof. Alternatively, the essential oil may be a basil, ylang-ylang, lime or sandalwood oil. Once the essential oil has been applied, the individual may touch, rub or press upon one or more of the tactile objects including, without limitation, rough spot 109 at Block 302. The application of the essential oil on the rough spot 109 helps to relax the senses of the individual touching the rough spot 109 at Block 303, which in turn helps to alleviate the individual's stress, anxiety, panic and the like.

Figure 4:
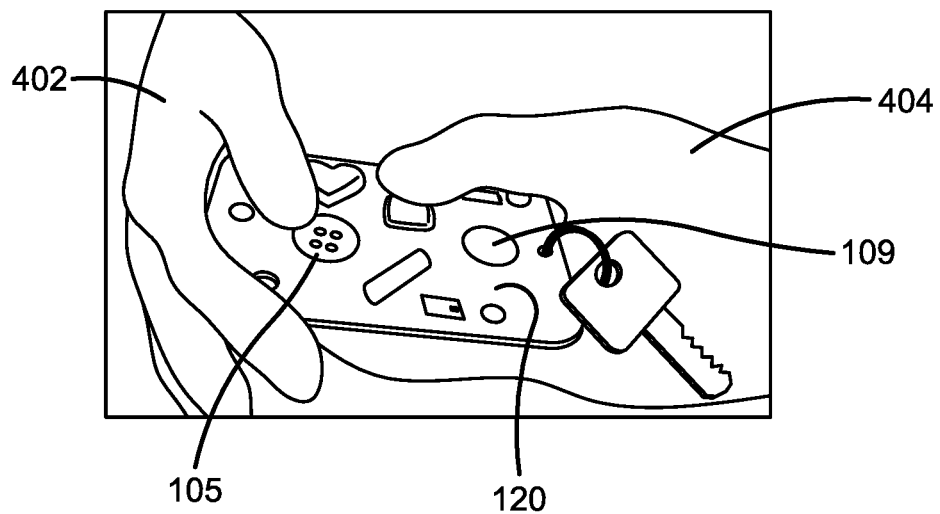
FIG. 4 illustrates a rear perspective view of one potential embodiment of the tactile platform or card of the present invention in accordance with the disclosed architecture, wherein the platform/card is being used by an individual.
Figure 6:
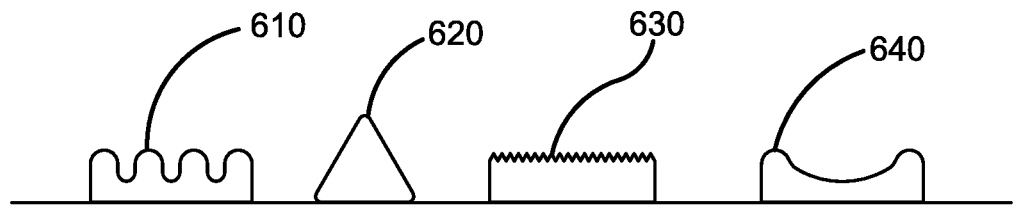
FIG. 6 illustrates an elevational view of one potential embodiment of the plurality of tactile objects attached to the rear surface of the platform or card of the present invention in accordance with the disclosed architecture.

FIG. 4 illustrates a rear perspective view of one potential embodiment of the tactile platform or card 100 of the present invention in accordance with the disclosed architecture, wherein the platform/card 100 is being used by an individual 500. As shown, the individual 500 may use his or her fingers of both hands 402, 404 to touch, rub and/or press on the tactile objects positioned along the rear surface 120 of the platform/card 100. In this manner, the tactile objects, such as the rough spot 109, curved button 105 with openings therein, gemstone 107 and others affixed to the surface 120, will alleviate the individual's tension, stress and anxiety by refocusing the individual's attention on the sensory perception of the objects and away from negative thoughts. Various other shapes of the tactile objects are shown in FIG. 6 and are discussed more fully below. One advantage of having a plurality of tactile objects having different textures and/or shapes is that the individual 500 can touch, rub and/or press the tactile object of his or her choice to create a different sensation. Further, the application of an essential oil to some or all of the tactile objects increases their effectiveness. The sensory touch of the tactile objects helps to alleviate the individual's tension and energy, thereby giving stress an outlet and helping to improve the concentration of the individual 500.

Figure 5:
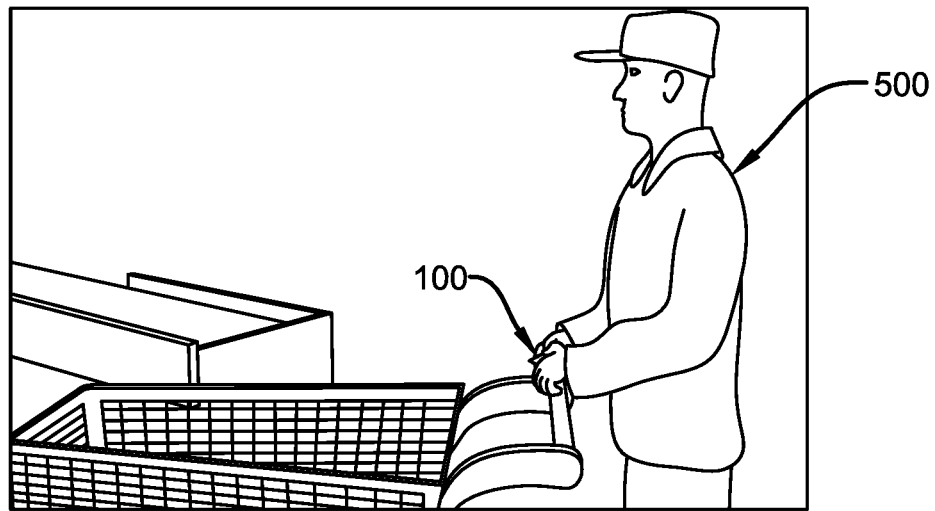
FIG. 5 illustrates a perspective view of one potential embodiment of the tactile platform or card of the present invention in accordance with the disclosed architecture, wherein the platform/card is being used by an individual in a public space, therefore showing the portability of the platform/card.

FIG. 5 illustrates a perspective view of one potential embodiment of the tactile platform or card 100 of the present invention in accordance with the disclosed architecture, wherein the platform/card 100 is being used by an individual 500 in a public space demonstrating the portability of the platform/card 100. As stated previously, the tactile platform/card 100 is fully portable and can be easily placed in a pocket or a purse so that the same is a readily available source of tactile stimulation to help relieve anxiety or stress. In one embodiment, the stress relieving card 100 can be attached with Velcro® or sewn to an object. The card 100 takes advantage of the skin being the individual's largest organ, and the calming stimulus provided by the tactile objects registers quickly and appropriately upon contact. In specific cases, such as Autism Spectrum Disorder, the card 100 is particularly useful because physical pressure helps minimize nervous responses and calms an individual suffering from overwhelming stimuli.

Pressing, rubbing and sliding of the fingers on the tactile objects helps to alleviate, or at least reduce, anxiety, PTSD, anger and other mental health conditions in a user. Further, tactile objects having a relatively rough surface cause uneven pressure on the skin when touched statically, and the inclusion of the gemstone 107 stimulates circulation of positive energy in the individual 500 using the tactile platform/card 100. The card 100 may be manufactured from a low density polyethylene (LDPE), and preferably exhibits low temperature flexibility, corrosion resistance, and good chemical and impact resistance.

FIG. 6 illustrates an elevational view of one potential embodiment of the plurality of tactile objects attached to the rear surface 120 of the platform or card 100 of the present invention in accordance with the disclosed architecture. Additional textures and shapes that may be used with the relaxation platform 100 include, but are not limited to, an undulating pattern 610, pointed shape 620, ridged pattern 630 and a recessed pattern 640. Nonetheless, many other configurations are of course possible depending on the needs and/or preferences of the individual 500. The plurality of elements disposed on the platform 100 can have any number of different tactile surfaces including, but not limited to, hard, soft, rough, smooth, pointed, recessed or ridged surfaces having a plurality of undulating peaks and valley and/or combinations thereof.

Figure 7:
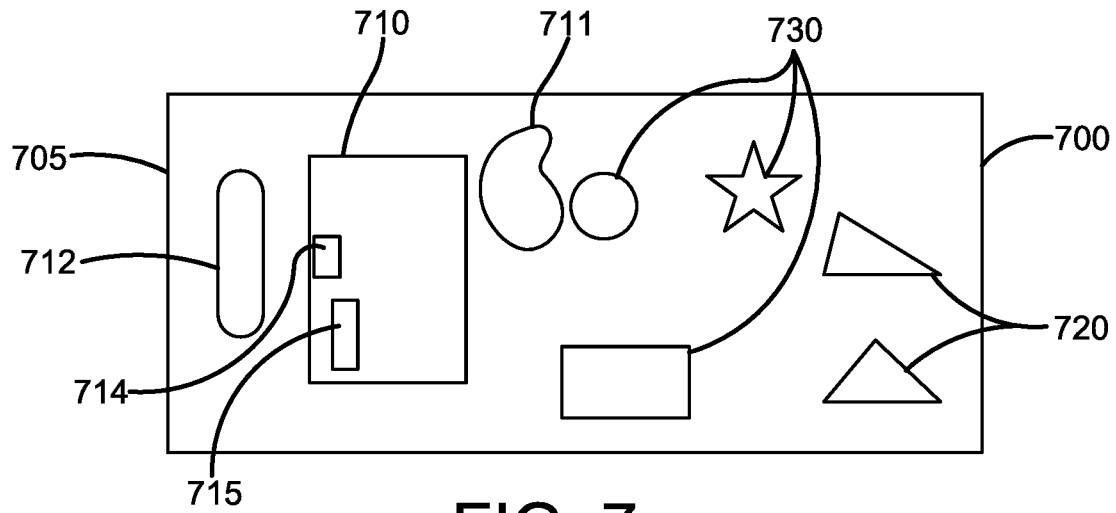
FIG. 7 illustrates a perspective view of one potential embodiment of a kit that can be used to personalize the tactile platform or card of the present invention in accordance with the disclosed architecture.

FIG. 7 illustrates a perspective view of one potential embodiment of a kit 700 that can be used to personalize the tactile platform or card 100 of the present invention in accordance with the disclosed architecture. In one embodiment, the kit 700 preferably includes a box or other package 705 for retail or online delivery, and one or more platform/cards 710 having first and second sides as described above. In addition, the kit 700 may also include a shaped element 711 to more easily be held in the palm of a user, and a compressible band 712 which may be applied to the perimeter of the card 710 or element 711 so as to make the perimeter of the card or relaxation platform softer when held by the individual 500. The kit 700 further includes a plurality of tactile elements 720, 730 that may comprise a variety of different shapes or surfaces for selection by the user. The elements 720, 730 may be attached to the platform/cards 710 or shaped element 711 by an adhesive, such as a removable adhesive 714, or by mechanical fasteners 715 which can be positioned at any point along the surface of the card 710 or shaped element 711. The kit 700 can be easily placed in a handbag, briefcase, glovebox or pocket for ready access during any stressful situation. Further, the tactile objects are preferably non-toxic, waterproof, free of BPAs, phthalates and latex.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein, "feel better card", "stress relieving card", "handheld physical card with attached tactile objects", "sensory tactile object card", and "tactile card" are interchangeable and refer to the tactile platform/card 100 of the present invention.

Notwithstanding the forgoing, the tactile platform/card 100 of the present invention and its various components can be of any suitable size and configuration as is known in the art without affecting the overall concept of the invention, provided that it accomplishes the above stated objectives. One of ordinary skill in the art will appreciate that the size, configuration and material of the tactile platform/card 100 and its components as shown in the FIGS. are for illustrative purposes only, and that many other sizes and shapes of the tactile platform/card 100 and its components are well within the scope of the present disclosure. Although the dimensions of the tactile platform/card 100 and its components are important design parameters for user convenience, the tactile platform/card 100 and its components may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A relaxation platform comprising:
   a shaped element having a central area and a perimeter, the central area having a front surface and a rear surface, wherein the front surface comprises an indicia and the rear surface contains a plurality of shaped items;
   the plurality of shaped items, wherein at least two of the plurality of shaped items have a different shape configuration and further wherein all of the plurality of shaped items are positioned within the perimeter;
   an essential oil; and
   at least one slot positioned on the front surface for holding an accessory attached to the shaped element.

2. The relaxation platform as recited in claim 1, wherein the shaped element is a card having a rigid central area.

3. The relaxation platform as recited in claim 1, wherein each of the plurality of shaped items has a tactile surface selected from a group consisting of a hard surface, a soft surface, a rough surface, a smooth surface, a pointed surface, a recessed surface, a ridged surface and a surface having undulating peaks and valleys.

4. The relaxation platform as recited in claim 1, wherein the shaped element comprises a NFC chip containing a set of information unique to a user.

5. The relaxation platform as recited in claim 4, wherein the set of information includes a set of medical and contact information.

6. The relaxation platform as recited in claim 1, wherein the shaped element comprises a speaker for playing a sound or a message contained in a memory module.

7. The relaxation platform as recited in claim 1, wherein the shaped element comprises a vibratory device.

8. The relaxation platform as recited in claim 1, wherein the essential oil includes at least one of a bergamot orange, a chamomile, a clary sage, a lavender, a neroli, a peppermint, a spearmint, a rosemary, a cedarwood, a sandalwood and a tea tree.

9. The relaxation platform as recited in claim 1 further comprising a battery for powering at least one of a speaker and a vibratory device.

10. The relaxation platform as recited in claim 1 further comprising a reservoir for holding the essential oil.

11. A tactile card comprising:
a card having a generally rectangular shape, a front surface and a rear surface;
at least one indicia positioned along the front surface;
a plurality of tactile elements positioned along the rear surface in spaced apart fashion; and
a slot for connecting the card to an accessory, wherein the plurality of tactile elements comprise at least a first type of tactile surface, a second type of tactile surface and a third type of tactile surface.

12. The tactile card as recited in claim 11, wherein each of the first, second and third tactile surfaces comprise a different one of a hard surface, a soft surface, a rough surface, a smooth surface, a pointed surface, a recessed surface, a ridged surface, and a surface having a plurality of undulating peaks and valleys.

13. The tactile card as recited in claim 12 further comprising a reservoir containing an essential oil.

14. The tactile card as recited in claim 13 further comprising at least one of a NFC chip, a speaker and a vibratory device.

15. The tactile card as recited in claim 14, wherein the card further includes a battery for powering the at least one of the NFC chip, the speaker or the vibratory device.

16. A kit for a sensory card comprising:
a package;
at least one card having a front surface and a rear surface;
a plurality of tactile elements for attachment to the at least one card;
a fastening means for attaching the plurality of tactile elements to the card, wherein the fastening means is selected from a group consisting of a mechanical fastener and an adhesive;
a battery; and
at least one of a vibratory mechanism and a speaker.

17. The kit as recited in claim 16 further comprising a memory module.

* * * * *